Figures 1, 2:
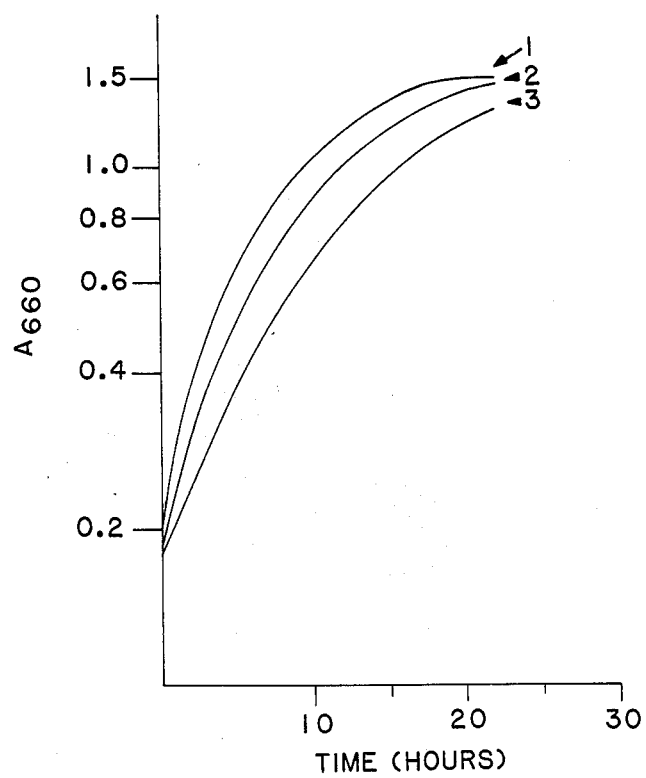

United States Patent [19]

Vandenbergh

[11] Patent Number: 4,800,158

[45] Date of Patent: Jan. 24, 1989

[54] BACTERIAL METHOD AND COMPOSITIONS FOR LINALOOL DEGRADATION

[75] Inventor: Peter A. Vandenbergh, Sarasota, Fla.

[73] Assignee: Microlife Technics, Inc., Sarasota, Fla.

[21] Appl. No.: 841,889

[22] Filed: Mar. 20, 1986

Related U.S. Application Data

[63] Continuation-in-part of Ser. No. 496,140, May 19, 1983, abandoned.

[51] Int. Cl.$^4$ .................. C12N 15/00; C12N 1/20; C07G 17/00; C12R 1/40
[52] U.S. Cl. .................. 435/172.1; 435/262; 435/267; 435/320; 435/876; 435/877; 435/252.34; 210/611; 210/908
[58] Field of Search .................. 435/253, 320, 172.1, 435/262, 267, 874, 876, 877, 172.3; 210/611, 908

[56] References Cited

U.S. PATENT DOCUMENTS 4,593,003 6/1986 Vandenbergh .................. 435/877

OTHER PUBLICATIONS

Mizutani et al., Nippon Nogei Kagaku Kaishi, 45(8), 1971, pp. 368-373, C.A. 76:11863d.
Murakami et al., Nippon Nogei Kagaku Kaishi, 47(11), 1973, pp. 699-703, C.A. 80:131634j.
Devi, et al., Indian J. Biochem. Biophys., 15(4), pp. 323-327, (1978), C.A. 90:99050j.
Devi et al., Indian J. Biochem. Biophys., 14(3), pp. 288-291, (1971), C.A. 88:18810r.
Chakrabarty et al., Proc. Nat. Acad. Science, U.S.A., 70, No. 4, 1137-1140, (1973).
Bensen et al., J. of Bacteriology, 126, 794-798, (1976).
Pemberton et al., Nature, 268, 732-733, (1977).
Bensen et al., J. of Bacteriology, 132, 614-621, (1977).
Vandenbergh et al., Applied and Environmental Microbiology, 42, 737-739, (1981).
Seubert W., J. Bacteriology, 79, 426-434, (1960).
Cantwell et al., J. Bacteriology, 135, 324-333, (1978).
Hansen et al., Nature, (London), 274: 715-717, (1978).
Madgastha et al., Canadian Journal of Microbiology, 23:230-239, (1977).
Renganathan et al., Applied and Env. Microbiol., 45:6-15, (1983).
Stanier et al., J. Gen. Microbiol., 43, 159-271, (1966).
Ish–Horowitz et al., Nuc. Acids Res., 9:2989-2998, (1981).
Olsen, R., J. Bacteriol., 133: 210-216, (1978).
Vandenbergh, et al., Appl. Envior. Microbiol., 46:128-132, (1983).

Primary Examiner—John Edward Tarcza
Assistant Examiner—Christopher Low
Attorney, Agent, or Firm—Ian C. McLeod

[57] ABSTRACT

A method for degrading linalool using Pseudomonas strains is described. Also described are novel *Pseudomonas putida* strains which degrade linalool and in some instances geraniol and citronellol. A method for producing 6-methyl-5-heptene-2-one using certain novel strains is also described.

17 Claims, 1 Drawing Sheet

A B C

BACTERIAL METHOD AND COMPOSITIONS FOR LINALOOL DEGRADATION

CROSS REFERENCE TO RELATED APPLICATION

The present invention is a continuation-in-part of application Ser. No. 496,140, filed May 19, 1983 now U.S. Pat. No. 4,593,003.

BACKGROUND OF THE INVENTION (1) Field of the Invention

The present invention relates to linalool metabolizing Pseudomonas strains including plasmid pSRQ60 which encodes for metabolism of linalool. In particular, the present invention relates to *Pseudomonas Putida* strains containing plasmid pSRQ60 and to a method for metabolizing linalool using such strains. The present invention also relates to producing a useful metabolite, i.e. 6-methyl-5-heptene-2one.

(2) Prior Art

The prior art has described various Pseudomonas strains which degrade aliphatic and aromatic compounds. In some instances the degradation is encoded by genes on a chromosome and in other instances by genes on a plasmid. Examples of such Pseudomonas strains are described by Chakrabarty et al. Proc Nat Acad Science USA 70 No. 4 1137–40 (1973); Bensen et al., J. of Bacteriology 126 794–798, (1976); Pemberton et al., Nature 268 732–733, (1977). Bensen et al., J. of Bacteriology 132 614–621, (1977) and Vandenbergh et al., Applied and Environmental Microbiology 42, 737–739, (1981).

The prior art has also described *Pseudomonas citronellolis* for degrading isoprenoids, particularly Seubert W. in J. Bacteriology 79 426–434 (1960) and Cantwell et al. in J. Bacteriology 135 324–333, (1978). *Pseudomonas Citronellolis* ATCC 13674 was surveyed for its extrachromosomal deoxyribonucleic acid (DNA) content, following the procedure of Hansen and Olsen, Nature (London) 274: 715–717 (1978). *P. Citronellolis* ATCC 13674 was observed to contain no resident plasmids. The metabolites of this strain do not include 6-methyl-5-heptene-b 2 one.

Linalool has the structure:

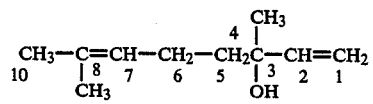

the numbered positions in the structure are not conventional but have been used in the literature.

Geraniol has the formula

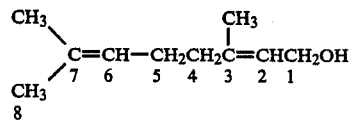

by conventional nomenclature it is 3,7-dimethyl-2-6 octadien-1-o1. The similarity of geraniol to linalool can be seen in relation to the position of the hydroxyl group. These compounds are characterized as isoprenoids and as an acyclic monoterpenes in view of their citrus fruit origins.

Madgastha et al, Canadian Journal of Microbiology 23:230–239 (1977) describe the metabolism of linalool by a Pseudomonas isolated from soil. This strain acted upon the 10 position of linalool to produce 10-hydroxy derivatives. There was no evidence of any oxidation of the 1 or 2 position of linalool.

Renganathan et al Applied and Env. Microbiol. 45:6–15 (1983) describes the metabolism of linalool and linalool derivatives by *Pseudomonas Incognita*. In this instance, the C-8 position is oxidized.

The pathways of degradation of linalool described by these later references does not involve the $C_1$ to $C_3$ carbon atoms. The degradative pathway for geraniol involves the formation of an enzyme intermediate. As can be seen from Cantwell, et al, the enzyme intermediate is formed by the elimination of acetic acid. This intermediate containing 9 carbon atoms is further oxidized and degraded. Thus the pathway involves the $C_1$ to $C_x$ sequentially carbon atoms.

OBJECTS

It is therefore an object of the present invention to provide Pseudomonas strains which have a unique ability to metabolize linalool. The present invention also relates to a method for producing 6-methyl-5-heptene-2 one which has a distinct fruity odor. Further still it is an object of the present invention to describe a method for the transfer of plasmids which encode for linalool metabolism to strains which metabolize geraniol and citronellol to make them more effective in degrading isoprenoids. These and other objects will become increasingly apparent by reference to the following description and to the Figures.

IN THE FIGURES

FIG. 1 shows an agarose gel electrophoresis of DNA preparation purified with cesium chloride-ethidium bromide. The agarose concentration was 0.7%, and migration was from top to bottom. Contents of lanes (from top to bottom) are as follows: (A) Parental strain *Pseudomonas fluorescens* PFL7.(pSRQ60/pSRQ41); bands: 60-Mdal plasmid covalently closed circular (CCC) DNA, 41-Mdal plasmid CCC DNA, and fragmented chromosomal DNA. (B) *Pseudomonas putida* PP0208 (pSRQ60); bands: 60-Mdal plasmid CCC DNA and fragmented chromosomal DNA. (C) *Pseudomonas putida* PPU2. (pSRQ60/pSRQ50/pSRQ80); bands: 80-Mdal plasmid CCC DNA, 60-Mdal plasmid CCC DNA, 50-Mdal plasmid CCC DNA, and fragmented chromosomal DNA.

FIG. 2 is a graph showing (1) growth of *Pseudomonas fluorescens* PFL7.(pSRQ60/pSRQ41) on minimal medium containing 0.3% linalool; (2) growth of *Pseudomonas putida* PPU2.9(pSRQ60/pSRQ50/pSRQ80) on minimal medium containing 0.3% linalool; and (3) growth of *Pseudomonas putida* PP0208 (pSRQ60) on minimal medium containing 0.3% linalool as a function of light transmission through the medium A660.

GENERAL DESCRIPTION

The present invention relates to a method for the metabolism of linalool as a pure chemical or in a natural or impure form with a bacterium of the genus Pseudomonas which comprises: metabolizing linalool with a strain of Pseudomonas containing plasmid pSRQ60 as carried in *Pseudomonas fluorescens* NRRL-B-18041, wherein the Pseudomonas has been cultured prior to being added to the linalool. The linalool concentration is usually less than about 0.5 percent by weight of the substrate containing it to allow growth.

The present invention also relates to the novel bacteria Pseudomonas putida NRRL-B-18040 (PPU2.9). This bacterium along with Pseudomonas fluorescens NRRL-B-18041 (PFL7.) Pseudomonas putida NRRL-B-15169 and 15172 described herein are deposited with the Northern Regional Research Laboratory in Peoria, Ill. and are freely available to those who request them by name and access number.

Further the present invention relates to a storage stable composition or culture which comprises at least about $10^8$ CFU per ml of a Pseudomonas putida containing the pladmid pSRQ60 as carried in Pseudomonas fluorescens NRRL-B-18041. To be practically useful, the composition to be supplied to users contains at least about $10^8$ CFU per ml up to about $10^{14}$ CFU per ml. Such compositions are not naturally occurring and generally are in the form of a culture which includes nitrogen and carbohydrate source and mineral nutrients for the bacteria and a preservation agent to maintain viability of the bacteria if they are to be stored before use. The composition can be in a preserved storage stable form such as lyophilized or frozen as is well known to those skilled in the art. The compositions can include other bacteria such as other organic compound utilizing strains, particularly Pseudomonas strains known to those skilled in the art.

Pseudomonas putida NRRL-B-18040 (PPU2.9) can be used to produce 6-methyl-5-hepten-2 one from geraniol or any natural material containing geraniol. The product has the formula:

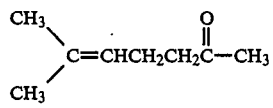

and is named by conventional nomenclature. The compound is an unsaturated ketone, has a pleasant fruity smell and can be used in foods. It is also polyfunctional and can be used in resins. Thus the present invention also relates to a method method for producing 6-methyl-5-hepten-2 one from geraniol which comprises: fermenting geraniol in a pure chemical form or in a natural or impure form in an aqueous growth medium containing a Pseudomonas putida containing plasmids pSRQ50 and pSRQ60 as carried in Pseudomonas putida NRRL-B-18040 (PPU2.9) to produce 6-methyl-5-hepten-2 one.

Finally the present invention relates to a method for producing a Pseudomonas putida which metabolizes citronellol, geraniol and linalool in a pure chemical form or in a natural or impure form which comprises: mating a Pseudomonas putida containing plasmid pSRQ60 as carried in Pseudomonas fluorescens NRRL-B-18041 with Pseudomonas putida NRRL-B-15169 containing plasmid pSRQ50 to produce a derived Pseudomonas putida containing plasmids pSRQ50 and pSRQ60.

SPECIFIC DESCRIPTION

In the following Examples, a bacterial strain was isolated from a waste water lagoon and identified as Pseudomonas fluorescens. This isolate was able to utilize linalool as sole carbon and energy source. This ability was found to be encoded on a 60-megadalton (60 Mdal) transmissible plasmid, pSRQ60. The plasmid was mated into a commercial waste treatment strain of Pseudomonas putida which metabolizes citronellol and geraniol to enhance its degradative ability by giving it the further capability of degrading linalool. The commercial strain Pseudomonas putida NRRL-B-15169 is described in U.S. patent application Ser. No. 496,140, filed May 19, 1983 by the inventor herein.

EXAMPLE 1

The isolation of a P. fluorescens strain capable of utilizing linalool as sole carbon and energy source and the presence of a transmissible plasmid that specifies its degradation is described.

Soil samples were obtained from the area surrounding a waste treatment lagoon from a turnpentine processor. The soil samples were inoculated into a minimal salts medium ($mm_o$) (Stanier, R. Y., et al, J. Gen. Microbiol. 43:159–271 (1966)) for liquid culture enrichment and incubated for 48 hours at 25° C. The medium contained linalool (0.3%) and yeast extract (0.05%). After incubation, portions of the enrichments were plated onto minimal medium containing linalool as sole carbon and energy source. A strain was obtained that was able to utilize linalool. The strain was purified and identified as P. fluorescens PFL7. as shown in Table 1.

TABLE 1

| Nutritional Properties of Bacterial Strains | | |
|---|---|---|
| Strain | Phenotype[a] | Deposit |
| P. fluorescens | | |
| PFL7.(pSRQ60/pSRQ41) | Prototroph, Lin[+b] | NRRL-B-18041 |
| PFL7.1(pSRQ60/pSRQ41) | Ura auxotroph, Lin[+] | |
| PFL7.2(pSRQ60/pSRQ41) | Leu auxotroph, Lin[+] | |
| P. putida | | |
| PPU2.(pSRQ50/pSRQ80) | Prototroph, Ger[+], Lin[−] | NRRL-B-15169 |
| PPU2.9(pSRQ60/pSRQ50/pSRQ80) | Prototroph, Ger[+], Lin[+] | NRRL-B-18040 |
| PPO208 | Trp auxotroph, Lin[−] | NRRL-B-15172 |
| PPO208(pSRQ60) | Trp auxotroph, Lin[+] | |

[a]Lin, linalool; Ger, geraniol; Ura, uradine; Leu, leucine; Trp, tryptophan; His, histidine; +, growth; −, no growth.
[b]Volatile carbon sources were supplied in the vapor phase in a sealed container. Incubation was for 48 hours at 25° C.

P. fluorescens PFL7. was examined for its extrachromosomal DNA content by the procedure of Ish-Horowitz and Barke (Ish-Horowitz, D. and J. F. Burke, Nuc. Acids Res. 9:2989–2998 (1981)). The isolation was found to contain 60-and 41-Mdal, resident plasmids, which were designated pSRQ60 and pSRQ41 respectively. The plasmid profile is shown in FIG. 1.

EXAMPLE 2

Mating experiments with P. fluorescens PFL7. were accomplished by the method of Olsen (Olsen, R. H., J. Bacteriol. 133:210–216 (1978)). The donors were auxotrophs obtained through mutagenesis with 1-methyl-3-nitro-1-nitrosoquanidine (Sigma Chemical Co., St. Louis, Mo.) by the procedure described in Vandenbergh et al (Vandenbergh, P. A., C. F. Gonzalez, A. M. Wright and B. S. Kunka. Appl. Environ. Microbiol. 46:128–132 (1983)).

The strain P. fluorescens PFL7.1(pSRQ60/pSRQ41) and PFL7.2 (pSRQ60/pSRQ41) were mated with recipient P. putida PPO208. P. putida PPO208 is a plasmid free strain which is unable to utilize linalool. The transconjugant P. putida PPO208(pSRQ60) was then successfully mated with *P. putida* PPU2.(pSRQ50/pSRQ80). The recipient *Pseudomonas putida* PPU2. in this mating is a commercial strain that degrades geraniol, but is unable to utilize linalool. The matings are shown in Table 1. Selection of linalool utilizing transconjugants was successful at various frequencies as shown in Table 2.

TABLE 2

| Transfer of the Linalool Plasmid | | | |
|---|---|---|---|
| Donor | Recipient | Selection[a] | Transconjugants Per Donor |
| PFL7.1(pSRQ41/ pSRQ60) | PPO208 | trp Lin | $3 \times 10^{-6}$ |
| PFL7.2(pSRQ41/ pSRQ60) | PPO208 | trp Lin | $2 \times 10^{-6}$ |
| PPO208 (pSRQ60) | PPU2.(pSRQ50/ pSRQ80) | Lin | $5 \times 10^{-6}$ |

These strains were checked for the expression of linalool metabolism and other markers.

The transconjugants were examined for their plasmid content and were observed to contain the 60 Mdal plasmid, pSRQ60 as shown by the plasmid profiles in FIG. 1. Growth studies were begun to check for the utilization of other $C_{10}H_{18}O$ isoprenoid substrates (Table 1). The transconjugants had acquired the ability to utilize linalool. Broth studies utilizing ($mm_o$) containing 0.3% linalool indicated that the transconjugants were able to utilize linalool at the same rate as compared to the parental strain *P. fluorescens* PFL7. (FIG. 2). An aliquot of the broth was filter sterilized and checked for the residual linalool at the completion of the growth experiment, on a Perkin Elmer 3920B utilizing a Supelco column GP5%SP-2100/0.1%SP-401. Based on comparisons of linalool standards, the linalool had been completely utilized.

The metabolism of linalool has been extensively investigated by Madgatha and Renganathan (Renganathan, V. and K. M. Madgastha., Appl. Environ. Microbiol. 45:6–15 (1983)) discussed above. Their isolate, *P. incognita*, grew slowly in the presence of 0.3% linalool as sole carbon and energy source. The presence of the 60 Mdal plasmid pSRQ60 enhances the degradative rate of the present strain. The substrate range of the commercial strain *Pseudomonas putida* NRRL-B-18040 (PPU2.9) was extended to include an additional isoprenoid, linalool. Also, the presence of this plasmid appeared to further enhance the utilization of geraniol in this commercial strain.

EXAMPLE 3

*Pseudomonas putida* PPU2.9(pSRQ60/pSRQ50/pSRQ80) was grown in minimal medium containing 0.3% geraniol, shaken at 250 rpm for 24 hours at 25° C. The strain containing this linalool plasmid was able to grow more efficiently in the presence of geraniol and it produced 6-methyl-5-Hetpen-2one as a by-product of the metabolism of geraniol. The compound was identified using Mass Spectral analysis.

As can be seen from the foregoing examples, unique strains of Pseudomonas have been produced using pSRQ60 which metabolizes linalool. At least some of the strains can metabolize geraniol to produce a useful product. Novel strains are described which have an enhanced ability to metabolize linalool, geraniol and citronellol. The strains herein can be mixed with known isoprenoid metabolizing strains for improved results.

It is intended that the foregoing description be only illustrative of the present invention and that the invention be limited only by the hereinafter appended claims.

I claim:

1. A method for the degradation metabolism of linalool as a pure chemical or in a natural or impure form with a derived Pseudomonas species which comprises: metabolizing linalool with a strain of Pseudomonas species as the derived Pseudomonas species containing plasmid pSRQ60 as carried in *Pseudomonas fluorescens* NRRL-B-18041, wherein pSRQ60 has been transferred to the derived Pseudomonas species from a parent Pseudomonas, wherein the Pseudomonas species has been cultured prior to being added to the linalool.

2. The method of claim 1 wherein the derived Pseudomonas species contains plasmids pSRQ50, pSRQ60 and pSRQ80 as carried in PSEUDOMONAS PUTIDA NRRL-B-18040 (PPU2.9).

3. The method of claim 1 wherein the parent Pseudomonas is a *Pseudomonas fluorescens* which contains plasmids pSRQ41 and pSRQ60 as carried in *Pseudomonas fluorescens* NRRL-B-18041(PFU 7.).

4. The method of claim 1 wherein the derived Pseudomonas species is a Pseudomonas putida containing pSRQ60 as a single plasmid.

5. The method of claim 1 wherein the derived Pseudomonas species is *Pseudomonas putida* PPO208(pSRQ60) and prototrophs or auxotrophs thereof differing from PPO208 (pSRQ60) only in nonessential compounds which are metabolized.

6. The method of claim 1 wherein the parent Pseudomonas is *Pseudomonas fluorescens NRRL-B*-18041 (PFL 7) and prototrophs or auxotrophs thereof differing from NRRL-B-18041 only in non-essential compounds which are metabolized.

7. The method of claim 1 wherein the derived Pseudomonas species is *Pseudomonas putida* NRRL-B-18040 (PPU 2.9) and prototrophs and auxotrophs thereof differing from NRRL-B-18040 only in non-essential compounds which are metabolized.

8. The method of claim 1 wherein the derived Pseudomonas species contains pSRQ50 and pSRQ60 as carried in *Pseudomonas putida* NRRL-B-18040(PPU2.9) and is mixed with an additional Pseudomonas strain which metabolizes isoprenoids.

9. The method of claim 8 wherein the additional Pseudomonas strain is *Pseudomonas citronellolis* ATCC 13674.

10. A storage stable biologically pure culture of *Pseudomonas putida* containing plasmid pSRQ60 as carried in *Pseudomonas fluorescens* NRRL-B-18041, wherein pSRQ60 has been transferred to the *Pseudomonas putida* from a parent Pseudomonas and auxotrophs and prototrophs of the derived *Pseudomonas putida* differing only in non-essential compounds which are metabolized.

11. The culture of claim 10 wherein the *Pseudomonas putida* is NRRL-B-15172 containing in addition the plasmid pSRQ60 and prototrophs or auxotrophs thereof differing from NRRL-B-15172 containing plasmid pSRQ60 only in non-essential compounds which are metabolized.

12. The culture of claim 10 wherein the *Pseudomonas putida* is NRRL-B-18040 (PPU 2.9) and prototrophs and auxotrophs differing from NRRL-B-18040 only in non-essential compounds which are metabolized.

13. A bacterium which comprises *Pseudomonas putida* NRRL-B-18040 (PPU 2.9) and auxotrophs and protorophs thereof, differing from NRRL-B-18040 only in non-essential compounds which are metabolized.

14. A bacterium which comprises a derived *Pseudomonas putida* containing plasmid pSRQ60 as carried in *Pseudomonas fluorescens* NRRL-B-18041 wherein pSRQ60 has been transferred to the *Pseudomonas putida* from a parent Pseudomonas and auxotrophs and protorophs of the derived *Pseudomonas putida,* differing only in non-essential compounds which are metabolized.

15. A method for producing a *Pseudomonas putida* which degradatively metabolizes citronellol, geraniol and linalool in a pure chemical form or in a natural or impure form which comprises:

mating a *Pseudomonas putida* containing pSRQ60 as carried in *Pseudomonas fluorescens* NRRL-B-18041 with *Pseudomonas putida* NRRL-B-15169 containing plasmid pSRQ50 to produce a derived *Pseudomonas putida* containing plasmids pSRQ50 and pSRQ60.

16. The method of claim 15 wherein the derived *Pseudomonas putida* is NRRL-B-18040(PPU2.9).

17. The method of claim 15 wherein the plasmid pSRQ60 is from *Pseudomonas fluorescens* NRRL-B-18041(PFL7.) which has been transferred to *Pseudomonas putida* NRRL-B-15169 by mating to produce *Pseudomonas putida* NRRL-B-18040.

* * * * *

UNITED STATES PATENT AND TRADEMARK OFFICE
CERTIFICATE OF CORRECTION

PATENT NO.  :  4,800,158
DATED       :  1989 January 24
INVENTOR(S) :  Peter A. Vandenbergh It is certified that error appears in the above—identified patent and that said Letters Patent is hereby corrected as shown below:

Title page:

Under "Other Publications" the date of the second Devi reference should be --(1977)-- rather than "(1971)".

Column 1, line 14 "metabilizing" should be --metabolizing--.

Column 1, line 45 "heptene-b 2 one." should be --heptene-2 one.--.

Column 2, line 62 "as" should be --in--.

Column 3, line 14 "pladmid" should be --plasmid--.

Column 3, line 30 "hepten" should be --heptene--.

Column 3, line 43, delete "method", first occurrence.

UNITED STATES PATENT AND TRADEMARK OFFICE
CERTIFICATE OF CORRECTION

PATENT NO. : 4,800,158
DATED : 1989 January 24
INVENTOR(S) : Peter A. Vandenbergh It is certified that error appears in the above—identified patent and that said Letters Patent is hereby corrected as shown below:

Column 3, line 44 "hepten" should be --heptene--.

Column 3, line 49 "hepten" should be --heptene--.

Column 4, line 14 "turnpentine" should be --turpentine--.

Column 4, line 49 "isolation" should be --isolate--.

Column 5, line 19 the footnote should be inserted as follows "aSelection was on minimal medium or amino acid supplemented medium containing the carbon source in the vapor phase. Incubation was for 48 hours at 25°C."

Column 5, line 59 "Hetpen" should be --heptene--.

Column 6, line 7 (Claim 1) "degradation" should be --degradative--.

Column 6, line 36 (Claim 6) "7)" should be "7.)"

Signed and Sealed this

Twenty-fifth Day of July, 1989

Attest:

DONALD J. QUIGG

Attesting Officer    Commissioner of Patents and Trademarks